US009826913B2

(12) United States Patent
Galea

(10) Patent No.: US 9,826,913 B2
(45) Date of Patent: *Nov. 28, 2017

(54) NON-INVASIVE INTRACRANIAL PRESSURE MONITORING SYSTEM AND METHOD THEREOF

(71) Applicant: Vivonics, Inc., Bedford, MA (US)

(72) Inventor: Anna M Galea, Stow, MA (US)

(73) Assignee: Vivonics, Inc., Bedford, MA (US)

( * ) Notice: Subject to any disclaimer, the term of this patent is extended or adjusted under 35 U.S.C. 154(b) by 939 days.

This patent is subject to a terminal disclaimer.

(21) Appl. No.: 13/939,824

(22) Filed: Jul. 11, 2013

(65) Prior Publication Data

US 2015/0018697 A1 Jan. 15, 2015

(51) Int. Cl.
*A61B 5/03* (2006.01)
*A61B 5/00* (2006.01)
*A61B 5/024* (2006.01)

(52) U.S. Cl.
CPC .......... *A61B 5/031* (2013.01); *A61B 5/02438* (2013.01); *A61B 5/6814* (2013.01); *A61B 5/6815* (2013.01); *A61B 5/6824* (2013.01); *A61B 5/6825* (2013.01); *A61B 5/6826* (2013.01); *A61B 5/7246* (2013.01); *A61B 5/7278* (2013.01); *A61B 5/742* (2013.01)

(58) Field of Classification Search
CPC ..... A61B 5/7278; A61B 5/031; A61B 5/6814; A61B 5/6826; A61B 5/6815; A61B 5/02438; A61B 5/7246; A61B 5/742

See application file for complete search history.

(56) References Cited

U.S. PATENT DOCUMENTS 5,527,822 A   6/1996   Scheiner
5,795,307 A   8/1998   Krueger
(Continued)

FOREIGN PATENT DOCUMENTS

WO   WO-2009/029386 A1 *   3/2009   ......... A61B 5/02007
WO   WO 2010/030612 A1   3/2010
WO   WO 2011103102 A1   8/2011

OTHER PUBLICATIONS

Van Santbrink et al., "Serial Transcranial Doppler Measurements in Traumatic Brain Injury With Special Focus on the Early Post-traumatic Period", Acta Neurochir, 2002, 144, pp. 1141-1149.
(Continued)

*Primary Examiner* — Meredith Weare
(74) *Attorney, Agent, or Firm* — Iandiorio Teska & Coleman, LLP

(57) ABSTRACT

A system which includes a first sensor placed proximate to a perfusion field of an artery receiving blood which emanates from the cranial cavity is configured to monitor pulsations of the artery receiving blood which emanates from the cranial cavity artery. A second sensor placed proximate to a perfusion field of an artery which does not receive blood emanating from the cranial cavity and approximately the same distance from the heart as the first sensor configured to monitor pulsations of the artery which does not receive blood emanating from the cranial cavity. A third sensor placed distally from a heart is configured to monitor pulsations of a distal artery. A processing system responsive to signals from the first, second, and third sensors is configured to determine intracranial pressure.

30 Claims, 11 Drawing Sheets

(56) References Cited

U.S. PATENT DOCUMENTS

| | | | |
|---|---|---|---|
| 5,997,484 A | 12/1999 | Sugahara | |
| 7,547,283 B2 | 6/2009 | Mourad et al. | |
| 8,211,031 B2 | 7/2012 | Poupko et al. | |
| 8,366,627 B2 | 2/2013 | Kashif et al. | |
| 8,394,025 B2* | 3/2013 | Ragauskas | A61B 5/031 600/437 |
| 8,512,260 B2 | 8/2013 | Grudic et al. | |
| 8,764,672 B2* | 7/2014 | Manwaring | A61B 5/027 600/506 |
| 2004/0087863 A1 | 5/2004 | Eide | |
| 2004/0260229 A1 | 12/2004 | Meir | |
| 2005/0119602 A1 | 6/2005 | Murphy et al. | |
| 2007/0213619 A1 | 9/2007 | Linder | |
| 2008/0077023 A1 | 3/2008 | Campbell et al. | |
| 2008/0287753 A1 | 11/2008 | Parlikar et al. | |
| 2008/0287812 A1 | 11/2008 | Parlikar | |
| 2008/0294057 A1 | 11/2008 | Parlikar et al. | |
| 2009/0143656 A1* | 6/2009 | Manwaring | A61B 5/026 600/324 |
| 2009/0234245 A1 | 9/2009 | Jaffe et al. | |
| 2010/0063405 A1 | 3/2010 | Kashif et al. | |
| 2010/0204589 A1* | 8/2010 | Swoboda | A61B 5/02007 600/485 |
| 2010/0210958 A1* | 8/2010 | Manwaring | A61B 5/027 600/506 |
| 2010/0331684 A1* | 12/2010 | Ragauskas | A61B 5/031 600/438 |
| 2011/0201962 A1 | 8/2011 | Grudic et al. | |
| 2012/0306884 A1 | 12/2012 | Parlikar et al. | |
| 2013/0006127 A1 | 1/2013 | Parlikar et al. | |
| 2013/0204139 A1 | 8/2013 | Kashif et al. | |
| 2013/0274615 A1* | 10/2013 | Ben-Ari | A61B 5/0205 600/483 |
| 2013/0289422 A1* | 10/2013 | Swoboda | A61B 5/02007 600/490 |
| 2016/0174858 A1* | 6/2016 | Galea | A61B 5/7278 600/473 |
| 2016/0192849 A1* | 7/2016 | Galea | A61B 5/031 600/473 |

OTHER PUBLICATIONS

Voss et al., "Posture-Induced Changes in Distortion-Product Otoacoustic Emissions and the Potential for Noninvasive Monitoring of Changes in Intracranial Pressure", Neurocritical Care, 2006, vol. 4, pp. 251-257.

Voulgaris et al., "Early Cerebral Monitoring Using the Transcranial Doppler Pulsatility Index in Patients With Severe Brain Trauma", Med. Sci. Monit., 2005, 11(2), www.MEDSCIMONIT.com, pp. CR49-CR52.

Deborah Warden, MD, "Military TBI During the Iraq and Afghanistan Wars", J. Head Trauma Rehabil., 2006, vol. 21, No. 5, pp. 398-402.

Zou et al., "Increased Phase Synchronization Between Intracranial Pressure and Arterial Blood Pressure During Elevated Intracranial Pressure in Dogs", Proceedings of the 2005 IEEE, Engineering in Medicine and Biology, 27th Annual Conference, Shanghai, China, Sep. 1-4, 2005, pp. 315-318.

Written Opinion of the International Searching Authority dated Mar. 3, 2015 for International Application No. PCT/US2014/00680 (six (6) pages total).

K. Kirk Shung, "Diagnostic Ultrasound. Imaging and Blood Flow Measurements", 2006, CRC Press, Taylor & Francis Group, Boca Raton, Florida.

B.A. Baldwin, "The Anatomy of the Arterial Supply to the Cranial Regions of the Sheep and Ox", Am. J. Anat., 1964, 115, pp. 101-117.

Blaivas et al., "Elevated Intracranial Pressure Detected by Bedside Emergency Ultrasonography of the Optic Nerve Sheath", Acad. Emerg. Med., Apr. 2003, vol. 10, No. 4, pp. 376-381.

Cernak et al., "Traumatic brain injury: an overview of pathobiology with emphasis on military populations", Journal of Cerebral Blood Flow & Metabolism, 2010, 30, 18 pages.

Davis et al., "Traditional Army Medical Wartime Structure", Chapter 2 of Army Medical Support for Peace Operations and Humanitarian Assistance, Prepared for the United States Army, Arroyo Center, RAND, 1996, pp. 5-14 (with 7 additional pages of Cover and Table of Contents) (17 pages total).

Geeraerts et al., "Ultrasonography of the optic nerve sheath may be useful for detecting raised intracranial pressure after severe brain injury", Intensive Care Med., 2007, 33, pp. 1704-1711.

Greenwald et al., "A Proposed Method to Reduce Underreporting of Brain Injury in Sports", Clin. J. Sport Med., Mar. 2012, vol. 22, No. 2, pp. 83-85.

R. Colin Johnson, "Blackbox Biometrics Testing ADI MEMS for Blast Gauge Monitor", EE Times, Connecting the Global Electronics Community, designlines Test & Measurement, Jun. 4, 2012, pp. 1-3.

Kety et al., "The Effects of Increased Intracranial Pressure on Cerebral Circulatory Functions in Man", Journal of Clinical Investigation (JCI), Received for Publication Dec. 4, 1947, pp. 493-499.

Lawrence Livermore National Laboratory, "Traumatic Brain Injury Protection: Blast Pressure Sensors in Helmets", Energy Innovation Portal, http://techportal.eere.energy.gov/technology.do/techID=512, May 10, 2011, 2 pages.

Manwaring et al., "Non-Invasive Sensor and Method for the Continuous Detection of Abnormal Intracranial Pressure and Brain Compliance", Oct. 16, 2013, http://jur.byu.edu/?p=7756, 2 pages.

Mazzola et al., "Critical Care Management of Head Trauma in Children", Crit. Care Med. 2002, vol. 30, No. 11 (Suppl.), pp. S393-S401.

Ommaya et al., "Causation, Incidence, and Costs of Traumatic Brain Injury in the U.S. Military Medical System", The Journal of Trauma; Injury, Infection, and Critical Care, Feb. 1996, .40(2), pp. 211-217 (12 pages total).

Querfurth et al., "Prediction of Intracranial Pressure From Noninvasive Transocular Venous and Arterial Hemodynamic Measurements", Neurocritical Care, 2004, vol. 1, pp. 183-194.

Ravi et al., "Intracranial Pressure Monitoring", Current Anaesthesia & Critical Care, 2003, 14, pp. 229-235.

Rutigliano et al., "Decompressive Craniectomy in Pediatric Patients With Traumatic Brain Injury With Intractable Elevated Intracranial Pressure", Journal of Pediatric Surgery, 2006, 41, pp. 83-87.

Schneier et al., "Incidence of Pediatric Traumatic Brain Injury and Associated Hospital Resource Utilization in the Unites States", Pediatrics, Aug. 2006, vol. 118, No. 2, pp. 483-492.

Shimbles et al., "Clinical Comparison of Tympanic Membrane Displacement With Invasive ICP Measurements", Acta Neurochir, 2005, (Suppl.), 95, pp. 197-199.

Simoens et al., "Arterial Supply to the Optic nerve and the Retina of the Sheep", J. Anat., 1981, 133, 4, pp. 481-497.

Bebout et al., "Detection of Hypoxemia During Peripheral Vasoconstriction at the Radial Artery and Various Pulse Oximeter Sensor Sites", Crit. Care. Med. 2003, 31(2), A72 (Abstract).

Frydrychowski et al., "Use of Near Infrared Transillumination/Back Scattering Sounding (NIR-T/BSS) to Assess Effects of Elevatedintracranial Pressure on Width of Subarachnoid Space and Cerebrovascular Pulsation in Animals", Acta. Neurobiol. Exp. (Wars), 2011, 71(3), pp. 313-321.

Leung et al., Investigation of Oxygen Saturation Derived from Cardiac Pulsations Measured on the Adult Head Using NIR Spectroscopy, Advances in Experimental Medicine and Biology, 2006, 578, pp. 209-215.

Phillips, Jeffrey B., "A Comparison of Near-Infrared Spectroscopy and Reflectance Sensors to Traditional Pulse Oximetry Under Conditions of Low Blood Oxygen Saturation", Naval Aerospace Medical Research Lab., Pensacola, FL, National Technical Information Service, No. 10-217, Jul. 21, 2010, 3 pgs.

Smielewski et al., "Clinical Evaluation of Near-Infrared Spectroscopy for Testing Cerebrovascular Reactivity in Patients With Carotid Artery Disease", Stroke, 1997, 28, pp. 331-338.

Townsend, Dr. Neil, "Pulse Oximetry", Medical, Electronics, Michaelmas Term, 2001, pp. 32-42.

(56) References Cited

OTHER PUBLICATIONS

Zweifel et al., "Noninvasive Monitoring of Cerebrovascular Reactivity With Near Infrared Spectroscopy in Head-Injured Patients", Journal of Neurotrauma, Nov. 2010, 27(11), pp. 1951-1958.

* cited by examiner

```
┌─────────────────────────────────────┐
│ Collect pressure pulsation information from │
│  • the supraobital artery or its capillary bed, and │
│  • an extracranial artery or its capillary bed │
│    approximately the same distance from the │
│    heart as the supraorbital artery, OR │
│  • a peripheral capillary bed │
│                  80                 │
└─────────────────────────────────────┘
                  │
                  ▼
┌─────────────────────────────────────┐
│ Obtain fourier                      │
│ transform information:              │
│ both magnitude and                  │
│ relative phase of each              │
│ component                           │
│              82                     │
└─────────────────────────────────────┘
                  │
                  ▼
┌─────────────────────────────────────┐
│ Compare the phase of each component. │
│ The phase of the components in the  │
│ supraorbital artery relative to the │
│ components of the other signal provides │
│ information on intracranial pressure │
│                 84                  │
└─────────────────────────────────────┘
```

*FIG. 6*

NON-INVASIVE INTRACRANIAL PRESSURE MONITORING SYSTEM AND METHOD THEREOF

GOVERNMENT RIGHTS

This invention was made with U.S. Government support under Contract No. N68335-10-C-0079, awarded by the Navy, and W81XWH-09-C-0118, awarded by the Army. The Government may have certain rights in certain aspects of the subject invention.

FIELD OF THE INVENTION

This invention relates to a non-invasive intracranial pressure monitoring system and method thereof.

BACKGROUND OF THE INVENTION

A closed-head brain injury, whether incurred as a result of blunt force trauma or a blast wave, can have insidious effects on a person. Although many casualties may suffer from headache or dizziness, it is difficult with conventional systems and methods to image every soldier or athlete in the field who experiences a potential brain injury. Most conventional imaging methods are large and require significant power. Moreover, damage to delicate brain tissues is frequently undetectable by conventional imaging, including CT scanning, even when such imaging is available.

The brain, however, is a soft organ with delicate structures held within a fixed volume. Damage to the small structures within a brain cause local swelling and cerebral blood flow and systemic blood pressure may not necessarily decrease with brain swelling. Therefore, even mild swelling of about 1 to 3 cc of extra fluid results in increased pressure. This elevated intracranial pressure (ICP) can itself cause more damage, including brain cell death and permanent brain injury or death.

In many active populations, especially true of the armed forces, or professional sports, a casualty may try to shrug off the seemingly mild symptoms of headache, dizziness, and the like. However, an unknown percentage of these injured are experiencing clinically significant elevated ICP which may worsen or result in permanent damage which could otherwise be avoided with the appropriate application of pharmacological or surgical interventions.

Currently, there is no known robust, portable, and reliable system or method which can accurately monitor ICP without direct access to the intracranial space. Therefore, it may not be feasible to check ICP on every person who has or may have experienced trauma to the brain. It is unknown how many casualties of blunt or blast trauma have underlying increased pressure in the brain that occurs in response to the injury.

The best conventional systems currently available to identify which casualties are at the most risk of brain injury are those that monitor the physical trauma (such as blast waves or impact) the head experiences. However, such conventional systems may only provide information based on an empirical diagnostic technique which may not take into account individual variability with regards to susceptibility of brain injury. Thus, two people experiencing the same physical trauma are likely to exhibit different levels of damage, but without a direct measure of the damage, they may be impossible to differentiate.

There are many conventional systems and methods that may hold promise for being able to measure or monitor ICP without direct access to the brain. These conventional systems and methods often employ large, heavy, power intensive equipment, such as MRI, and the like, and therefore are not portable. This limits their use in the battlefield or at the sidelines in sports related injuries.

The supraorbital artery provides an avenue of information from the cranial cavity. This vessel emanates from the internal carotid artery via the orbit and is readily accessible at the forehead. By virtue of its path along the periphery of the brain, it carries with it information related to the ICP. U.S. Pub. No. 2009/0143656 to Manwaring et al., discloses that the supraorbital artery may be used to determine ICP. However, as disclosed therein, only two sensors are used which may limit the accuracy of the measured ICP. Moreover, to date no practical device has emerged from the '656 patent application.

Thus, there is a need for a system and method that can measure ICP noninvasively, unobtrusively and continuously to provide an accurate measure of the extent of brain injury and enable medical care to timely provide the needed care. Moreover, in cases where the injury might have gone undetected until extensive damage has been done due to unchecked swelling, there is a need for effective threat agent that more quickly resolves the problem and returns the injured person to work, a soldier to duty, or a athlete to top performance.

SUMMARY OF THE INVENTION

In one aspect, a non-invasive intracranial pressure monitoring system is featured. A first sensor placed proximate to a perfusion field of an artery receiving blood which emanates from the cranial cavity is configured to monitor pulsations of the artery receiving blood which emanates from the cranial cavity artery. A second sensor is placed proximate to a perfusion field of an artery which does not receive blood emanating from the cranial cavity and placed approximately the same distance from the heart as the first sensor configured to monitor pulsations of the artery which does not receive blood emanating from the cranial cavity. A third sensor placed distally from the heart is configured to monitor pulsations of a distal artery. A processing system responsive to signals from the first, second, and third sensors is configured to determine intracranial pressure.

In one embodiment, the first sensor may be placed on the forehead. The second sensor may be placed on or near the temple on or near the ear. The third sensor may be placed distally on a finger, on a hand, or on a forearm. The processing subsystem may be configured to determine the intracranial pressure by correlating signals from the first sensor to signals from the third sensor and correlating signals from the second sensor to signals from the third sensor and combining the determined correlations. The processing subsystem may be configured to determine the intracranial pressure by determining the magnitude and phase of the spectral components of signals from each of the first, second, and third sensors and comparing the magnitude or the phase of the spectral components of the first sensor to the magnitude or the phase of the spectral components of third sensor and the magnitude or the phase of the spectral components of the second sensor to the magnitude or the phase components of the third sensor and combining the compared values. The processing subsystem may be configured to adjust the value of the component phases according to differences in magnitudes of associated spectral components. The processing subsystem may be configured to determine the intracranial pressure by combining the signals from the first sensor with the signals from the second sensor and combining the result with the signals from the third sensor. The system may include a display coupled to the processing subsystem configured to display the intracranial pressure.

In another aspect, a non-invasive intracranial pressure monitoring system is featured. A first sensor placed proximate to the supraorbital artery is configured to monitor pulsations of the supraorbital artery. A second sensor placed proximate to a branch of the external carotid artery and placed approximately the same distance from the heart as the first sensor is configured to monitor pulsations of the external carotid artery. A third sensor placed distally from the heart is configured to monitor pulsations of a distal artery. A processing subsystem responsive to signals from the first, second, and third sensors is configured to determine intracranial pressure.

In another embodiment, the first sensor may be placed on the forehead. The second sensor may be placed on or near the temple, or near the ear. The third sensor may be placed distally on a finger, or on a hand, or a forearm. The processing subsystem may be configured to determine the intracranial pressure by correlating signals from the first sensor to signals from the third sensor and correlating signals from the second sensor to signals from the third sensor and combining the determined correlations. The processing subsystem may be configured to determine the intracranial pressure by determining the magnitude and phase of the spectral components of signals from each of the first, second, and third sensors and comparing the magnitude or the phase of the spectral components of the first sensor to the magnitude or the phase of the spectral components of the third sensor and the magnitude or the phase of the spectral components of the second sensor to the magnitude or the phase of the spectral components of the third sensor and combining those compared values. The processing subsystem may be configured to adjust the value of the component phases according to differences in magnitudes of associated spectral components. The processing subsystem may be configured to determine the intracranial pressure by combining signals from the first sensor with the signals from the second sensor and combining the result with signals from the third sensor. The system may further include a display coupled to the processing subsystem configured to display the intracranial pressure.

In one aspect, a method for non-invasively determining intracranial pressure is featured. The method includes monitoring pulsations of an artery receiving blood which emanates from the cranial cavity and generate first output signals, monitoring pulsations of an artery which does not receive blood emanating from the cranial artery and generates second output signals, monitoring pulsations of a distal artery and generates third output signals, and n response to the first, second and third output signals, determining the intracranial pressure.

In one embodiment, the monitoring pulsations of blood which emanates from the cranial artery may be performed proximate a forehead. The monitoring pulsations of blood which does not emanate from a cranial artery may be performed on or near the temple or on or near the ear. The monitoring pulsations of the distal artery may be performed on a finger, on a hand, or on a forearm. Determining the intracranial pressure may include correlating the first output signals to the third output signals and correlating the second output signals to the third output signals and combining the determined correlations determining the intracranial pressure may include determining the magnitude and phase of spectral components of each of the first output signals, the second output signals, and the third output signals and comparing the magnitude or the phase of the spectral components of the first output signals with the magnitude or the phase of the spectral components of the third output signals and the magnitude or the phase of the spectral components of the second output signals to the magnitude or the phase of the spectral components of the third output signals and combining the compared values. The method may further include adjusting the value of component phases according to differences in magnitudes of associated spectral components. Determining the intracranial pressure may include combining the first output signals with the second output signals and combining that result with the third output signals.

In another aspect, a non-invasive method for determining intracranial pressure is featured. The method includes monitoring pulsations of the supraorbital artery and generates first output signals, monitoring pulsations of the external carotid artery and generate second output signals, monitoring pulsations of the distal artery and generate third output signals, and in response to the first, second, and third output signals determining the intracranial pressure.

In one embodiment, monitoring pulsations of the supraorbital artery may be performed on the forehead. Monitoring pulsations of the external carotid artery may be performed on or near the temple, or on or near the ear. Monitoring pulsations of the distal artery may be performed on a finger, on a hand, or on a forearm. Determining the intracranial pressure may include correlating the first output signals to the third output signals and correlating the second output signals to the third output signals and combining the determined correlations. Determining the intracranial pressure may include determining the magnitude and phase of spectral components of each of the first output signals, the second output signals, and the third output signals and comparing the magnitude or the phase of the spectral components of the first output signals with the magnitude or the phase of the spectral components of the third output signals and the magnitude or the phase of the spectral components of the second output signals to the magnitude or the phase of the spectral components of the third output signals and combining the compared values. The method may further include adjusting the value of component phases according to differences in magnitudes of associated spectral components. The method in which determining the intracranial pressure may include combining the first output signals with the second output signals and combining that result with the third output signals.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 6 is flow chart showing the primary steps of another embodiment of the method for non-invasively determining the intracranial pressure monitoring of this invention;

DETAILED DESCRIPTION OF THE INVENTION

Figure 1:
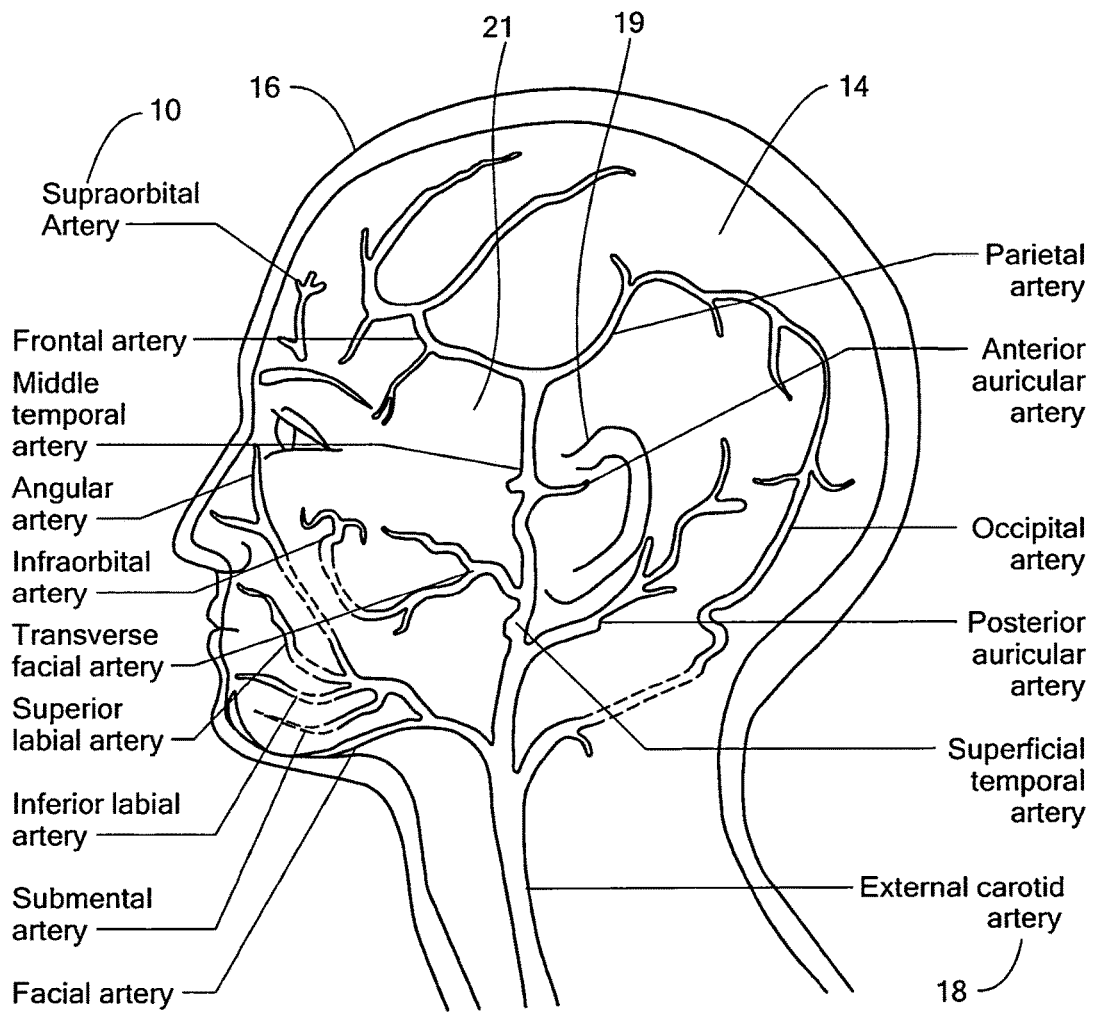
FIG. 1 shows a depiction of a vasculature of the human head.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of the vasculature of the human head. One key vasculature often used in determining ICP is supraorbital artery 10. Supraorbital artery 10 is an example of an artery which receives a flow of blood which emanates from within cranial cavity 14. As can be seen, supraorbital artery 10 is proximate forehead 16 of the skull. External carotid artery 18 is another artery often used to determine ICP. External carotid artery 18 is branched as shown and is an example of an artery which does not receive blood which emanates from cranial cavity 14. External carotid artery 18 is located proximate to ear 19 or temple 21.

Figure 2:
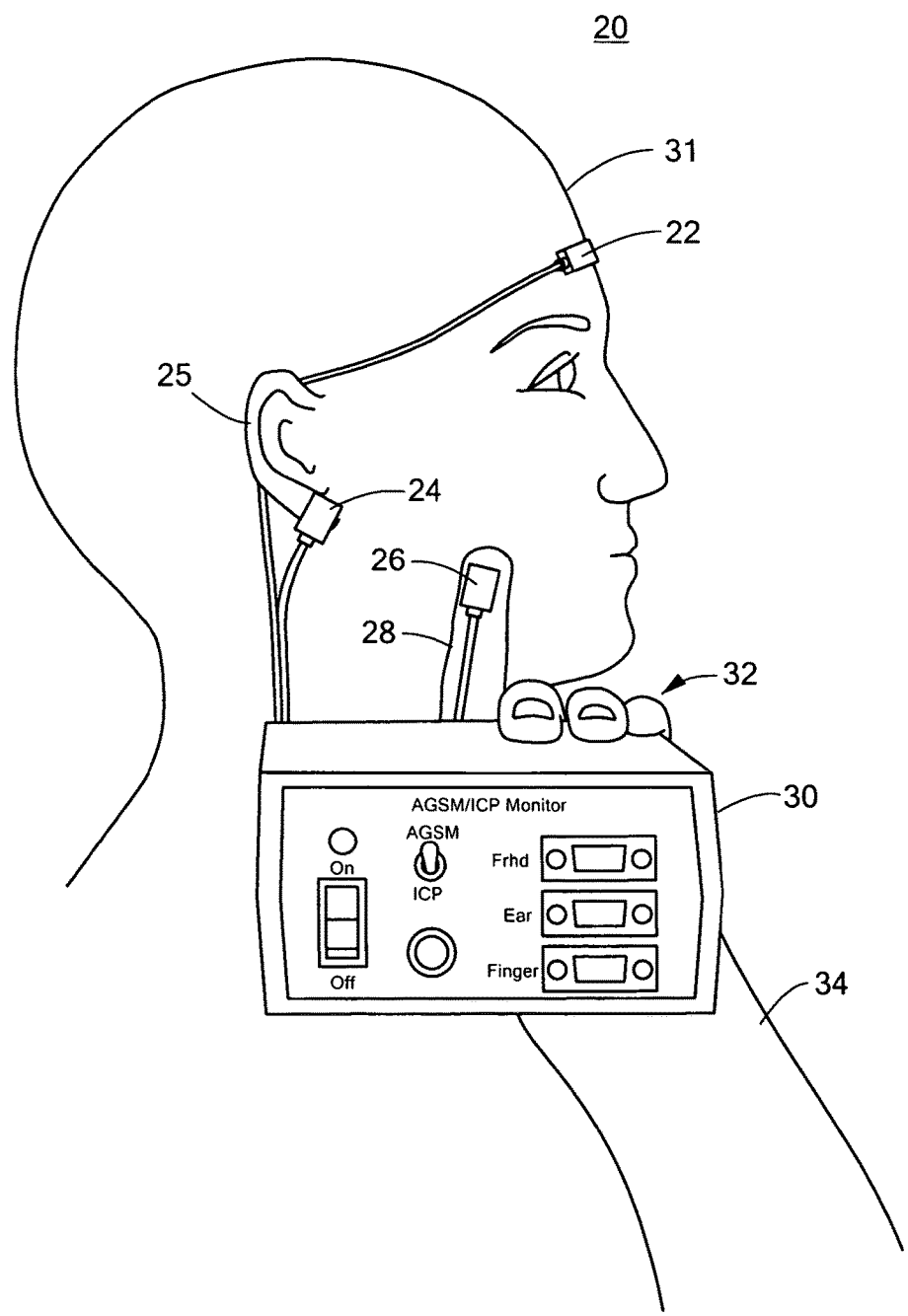
FIG. 2 is a three-dimensional view showing the primary components of one embodiment of the non-invasive intracranial pressure monitoring system and method thereof of this invention.

Non-invasive intracranial pressure monitoring system 20, FIG. 2, of one embodiment of this invention, includes first sensor 22 placed proximate a diffusion field of an artery receiving blood which emanates from within cranial cavity 14, FIG. 1, and is configured to monitor pulsations of that artery. In one example, the diffusion field is a capillary bed and the artery receiving blood which emanates from the cranial cavity is supraorbital artery 10. In this example, sensor 22, FIG. 2, is placed proximate forehead 31 as shown, which is near supraorbital artery 10, FIG. 1, as discussed above.

Non-invasive intracranial pressure monitoring system 20, FIG. 2, also includes second sensor 24 placed proximate a perfusion field of an artery which does not receive blood emanating from cranial cavity 14 and is configured to monitor pulsations that artery. Second sensor 24 is placed approximately the same distance from the heart (not shown) as first sensor 22. In this example, the diffusion field is a capillary bed and the artery receiving blood which does not emanate from the cranial cavity is external carotid artery 18, FIG. 1. In this example, sensor 24 is placed proximate ear 25 as shown, e.g., on the ear lobe, which is near external carotid artery 18. In other examples, second sensor 24 may be placed on or near the temple 21.

Non-invasive intracranial pressure monitoring system also includes third sensor 26 placed distally from the heart configured to monitor pulsations of a distal artery. For example, third sensor 26 may be placed on finger 28 which is located near one or more distal arteries inside finger 28. In other examples, third sensor may be placed on the hand 32, forearm 34, or any other desired distal location.

Non-invasive intracranial pressure monitoring system 20 also includes processing subsystem 30 responsive to signals from first sensor 22, second sensor 24, and third sensor 26 that include data on the monitored pulsations of the artery receiving blood which emanates from the cranial cavity, the artery receiving blood which does not emanate from the cranial cavity, and the distal artery, respectively to determine the inner cranial pressure.

Figure 3:
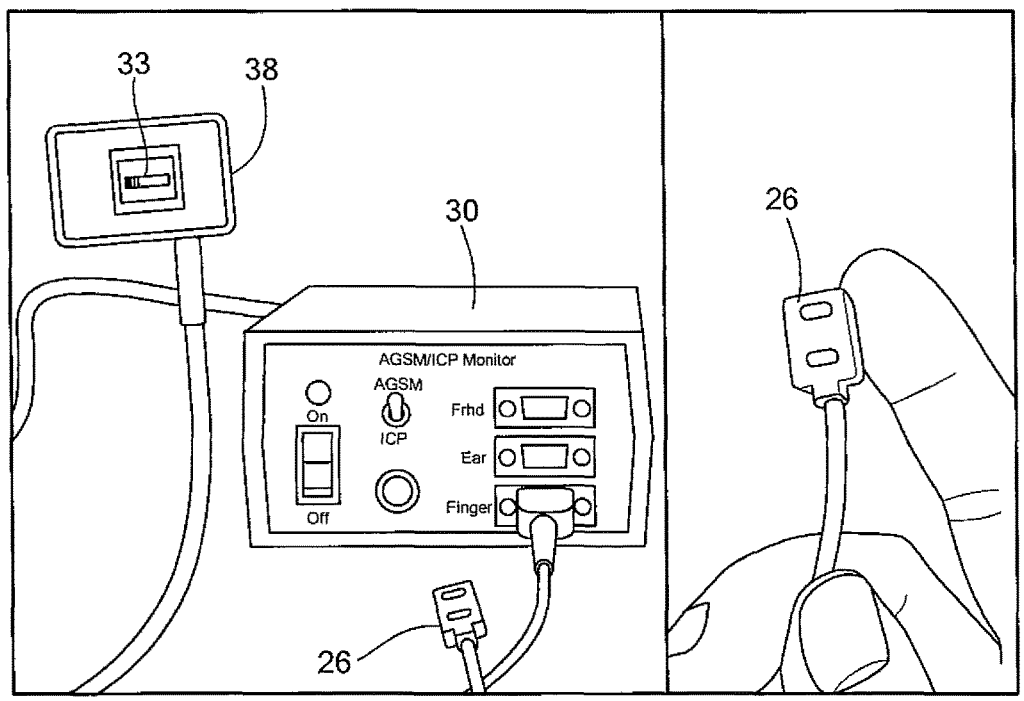
FIG. 3 is a photograph showing an enlarged view of the processing subsystem and the third sensor shown in FIG. 2.

FIG. 3 shows an enlarged view of processor subsystem 30 and enlarged view of third sensor 26 coupled to processing subsystem 30. Preferably, first sensor 22, FIG. 2, second sensor 24 and/or third sensor 26 are near infrared (NIR) type sensors. System 20 also preferably includes monitor 38, FIG. 3, e.g., small LCD screen 33 configured to display and provide real-time feedback of the determined intracranial pressure values.

Non-invasive intracranial pressure monitoring system 20 preferably uses first sensor 22, second sensor 24, and third sensor 26 to extract the information needed from the perfusion field of the supraorbital artery, the external carotid artery, a distal artery, and other vasculature. The data from the supraorbital artery provided by first sensor 22 may be analyzed with data obtained from an identical second sensor 24 on a perfusion field of the external carotid artery, either on the ear lobe (auricular artery) of ear 25 or on temple 21 (temporal artery). These locations are at a comparable distance from the heart as supraorbital artery 10. Therefore, the external carotid signal from second sensor 24 can be used to exclude the part of the signal that stems from whole body vascular resistance and pressure. Non-invasive intracranial pressure monitoring system 20, FIG. 2, also utilizes third sensor 26 placed on the finger or other part of the body as a reference for signals from first sensor 22 and second sensor 24.

The result is non-invasive intracranial pressure monitoring system 20 that non-invasively, accurately, efficiently, effectively, and continuously determines ICP. System 20 is small, robust, light weight and utilizes very little power. In one example, system 20 may be able to run for a full day using 4 AA batteries. Thus, system 20 is portable and can be used in the battlefield, in the field for sports related injuries, or any similar type situation, to provide an accurate measure of ICP to determine the extent of brain injury and enable medical care to timely provide the needed care.

The algorithm for non-invasive intracranial pressure monitoring system 20 and methods thereof discussed below are preferably based on relative time lags between the supraorbital artery and the external carotid artery. First sensor 22, second sensor 24, and third sensor 26, preferably NIR sensors, provide signals, based on the strength of the reflectance of the subtended tissue at the NIR frequency range that increases when a pulse passes through the monitored perfusion bed. Recording this signal optically, using NIR sensors, proves to be more robust and less sensitive to sensor placement or motion artifact than tonometry-based systems.

Non-invasive intracranial pressure monitoring system 20 preferably operates on the principle that a less compliant vascular tree propagates a pressure wave faster than a more compliant tree. Increased pressure surrounding the vessels, such as the pressure in the cranium surrounding the internal carotid effectively stiffens the vasculature. Therefore, a pressure wave in the internal carotid will traverse the cranial vault faster than the same wave traveling in the external carotid. The difference between the two may be very small, and in accordance with system 20, is preferably more robust to compare each to a distal signal provided by third sensor 26, e.g., located on the finger, and then compare the two differences.

In one embodiment, processing subsystem 30 is configured to determine the intracranial pressure by determining the magnitude and phase of the spectral components of signals from each of first sensor 22, second sensor 24, and third sensor 26, by comparing the magnitude or the phase of the spectral components of first sensor 22 to the magnitude or the phase of the spectral components of third sensor 26 and the phase of the spectral components of second sensor 24 to the magnitude or the phase of the spectral components of third sensor 26 and combining the compared values. In one example, processing subsystem 30 is configured to adjust the value of the component phases according to differences in the magnitudes of the associated spectral components. See FIG. 8 (discussed below).

In another embodiment, processing subsystem 30 is configured to determine the intracranial pressure by correlating signals from first sensor 22 to signals from third sensor 26 and correlating signals from second sensor 24 to third sensor 26 and combining the determined correlations. See FIG. 8 (discussed below).

In yet another embodiment, processing subsystem 30 is configured to determine the intracranial pressure by combining signals from first sensor 22 with signals from second sensor 24 and combining that result with signals from third sensor 26. See FIG. 9 discussed below.

Figure 4:
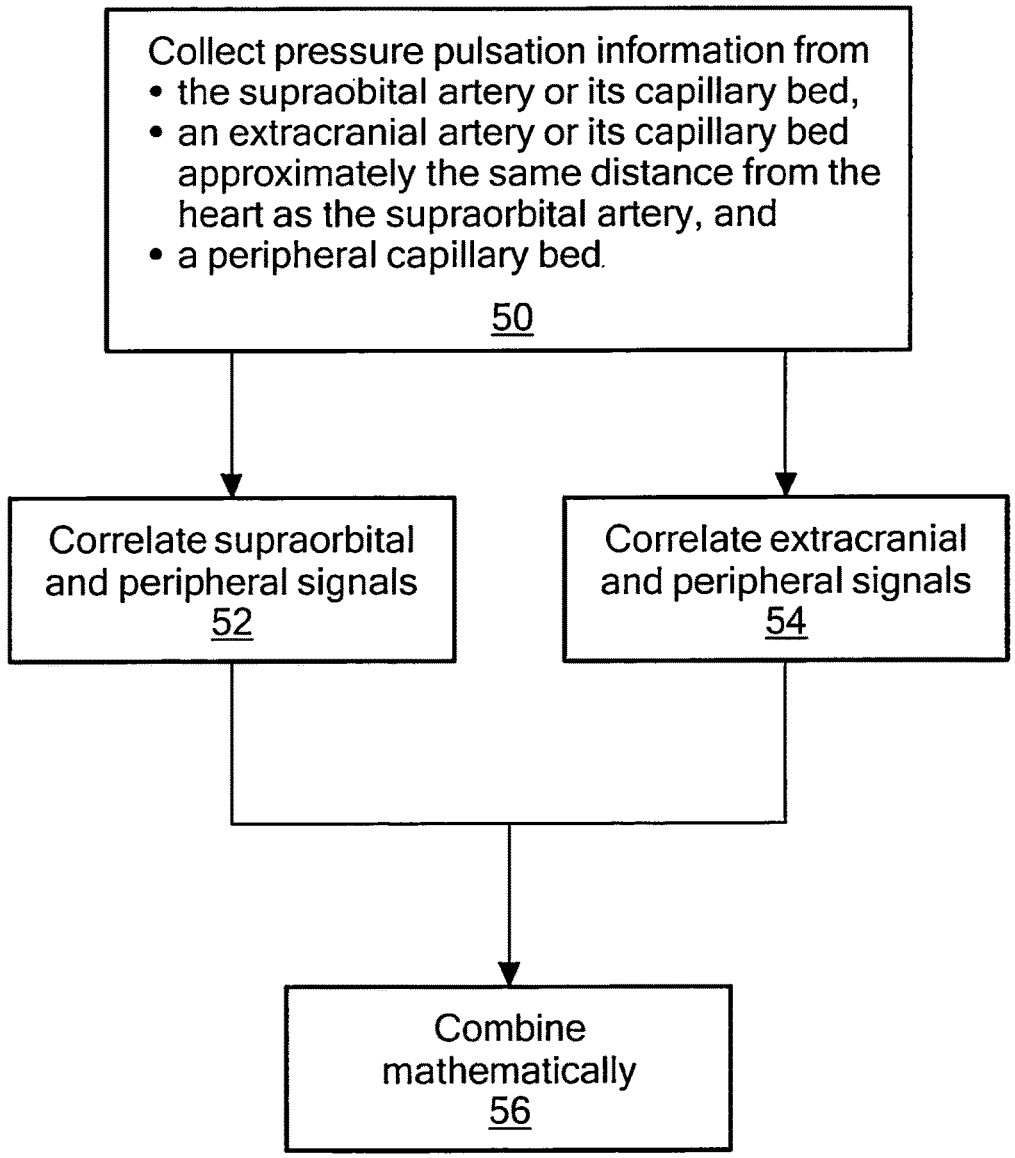
FIG. 4 is flow chart showing the primary steps of one embodiment of the method for non-invasively determining the intracranial pressure monitoring system of this invention.

FIG. 4 shows a flowchart of one embodiment of the method of determining intracranial pressure using non-invasive intracranial pressure monitoring system 20, FIG. 2, in accordance with one embodiment of this invention. In this example, pulsations of the supraorbital artery 10, FIG. 1, are monitored by first sensor 22, FIG. 2 placed on forehead 31, pulsations of external carotid artery monitored by second sensor 24 placed proximate ear 25, and a pulsation of distal artery are monitored by third sensor 26 placed proximate finger 28, step 50. Signals from first sensor 22 to the third sensor 26 are correlated, step 52. Signals from second sensor 24 and the third sensor are then correlated, step 54. The signals from steps 52 and 54 are combined mathematically to determine ICP, step 56. See FIG. 8. Flow chart 58, FIG. 5 shows a more detailed specific implementation of the method shown in FIG. 4.

FIG. 6 shows a flowchart of another embodiment of the method of determining intracranial pressure using non-invasive intracranial pressure monitoring system 20, FIG. 2, in accordance with another embodiment of this invention. In this example, pulsations of the supraorbital artery 10, FIG. 1, are monitored by first sensor 22, FIG. 2, placed on forehead 31, pulsations of external carotid artery 18 are monitored by second sensor 24 placed proximate ear 25, and a pulsation of the distal artery are monitored by third sensor 26 placed proximate finger 28, step 80. Processing subsystem 30, FIG. 2, responsive to the signals from first sensor 22, second sensor 24, and third sensor 26, performs a Fourier transform to determine the magnitude and phase of spectral components of signals output from each of first sensor 22, second sensor 24, and third sensor 26, step 82. The phase of the spectral components of first sensor 22 is compared to the phase of the spectral components of third sensor 26 and the phase of the spectral components of second sensor 24 is compared to the phase of the spectral components of third sensor 26, and the values are combined to determine ICP, step 84, FIG. 6. See FIG. 8. Preferably, processing subsystem 30, FIG. 3, is configured to adjust the value of the component phases according to differences in magnitudes of associated spectral components.

Figure 7:
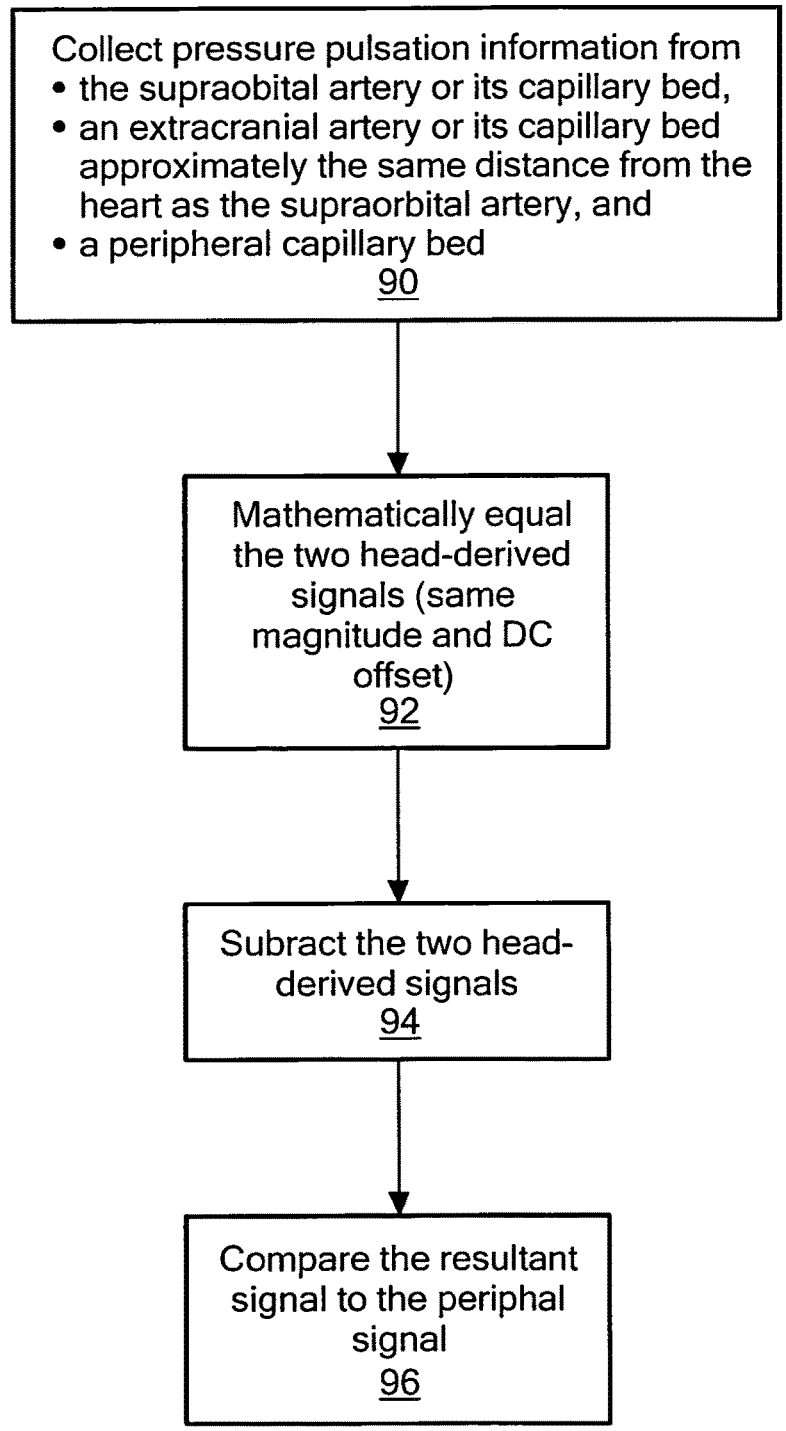
FIG. 7 is flow chart showing the primary steps of yet another embodiment of the method for non-invasively determining the intracranial pressure monitoring system of this invention.

FIG. 7 shows a flowchart of another embodiment of the method of determining intracranial pressure using non-invasive intracranial pressure monitoring system 20, FIG. 2, in accordance with another embodiment of this invention. In this example, pulsations of the supraorbital artery 10, FIG. 1, are monitored by first sensor 22, FIG. 2, placed on forehead 31, pulsations of external carotid artery 18 are monitored by second sensor 24 placed proximate ear 25, and a pulsation of distal artery are monitored by third sensor 26 placed proximate finger 28, step 90, FIG. 7. Processing subsystem 28 is configured to determine the intracranial pressure by combining signals that are mathematically equal in at least one mathematical measure, such as offset value or maximum value from first sensor 22 with signals from second sensor 24, step 92. The result of step 92 is combined with signal from third sensor 26, step 96. See FIG. 9.

Figure 5:
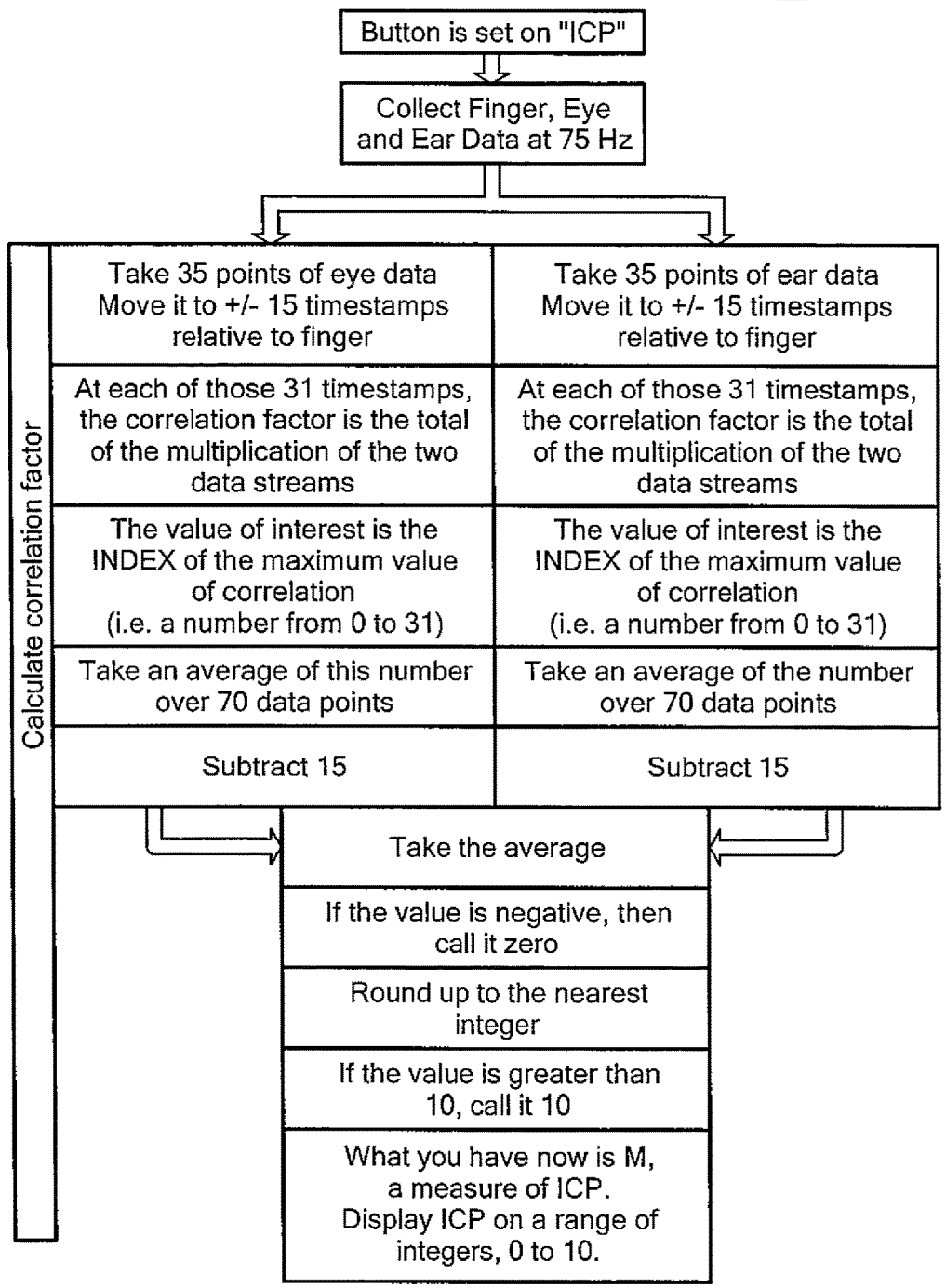
FIG. 5 is flow chart showing in further detail the steps of method for non-invasively determining the intracranial pressure monitoring system shown in FIG. 4.
Figure 8:
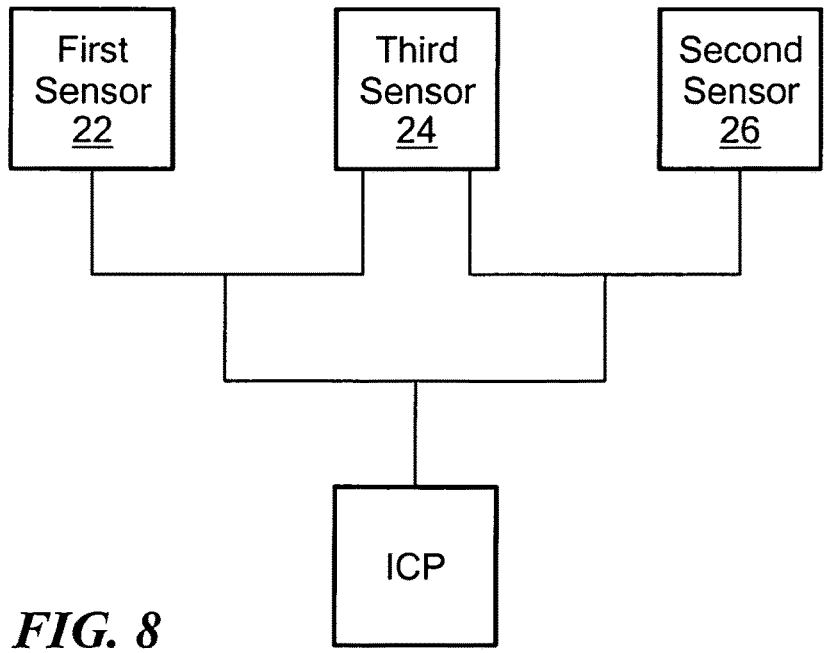
FIG. 8 is a schematic block diagram overview showing the primary components used by the method for non-invasively determining the intracranial pressure shown in FIGS. 4-6.
Figure 9:
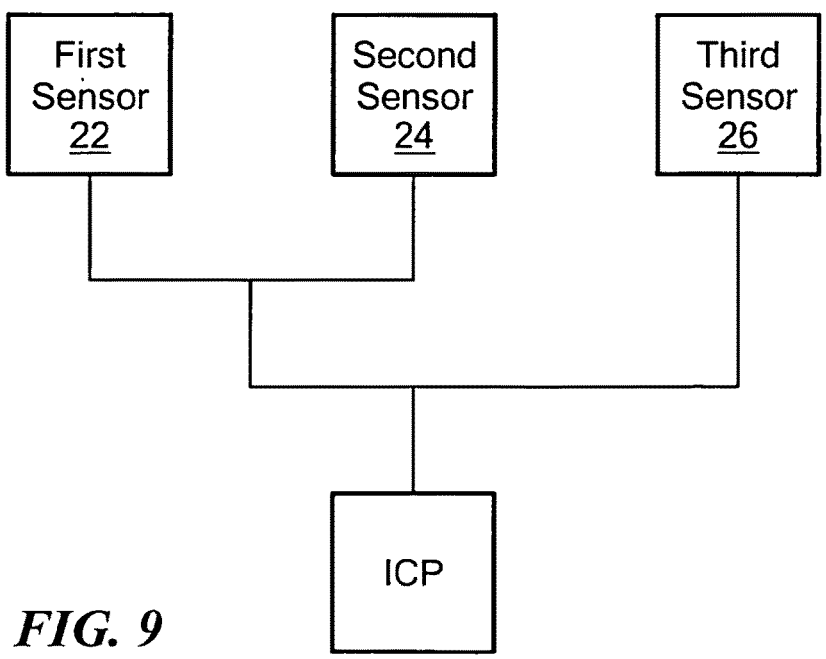
FIG. 9 is a schematic block diagram overview showing the primary components used by the method for non-invasively determining the intracranial pressure shown in one or more of FIG. 7.

FIG. 8 shows a schematic block diagram overview of the primary steps associated with the method of determining intracranial pressure using non-invasive intracranial pressure monitoring system 20, FIG. 2, shown in FIGS. 4-6. FIG. 9 shows a schematic block diagram overview of the primary steps associated with method of determining intracranial pressure using non-invasive intracranial pressure monitoring system 20, FIG. 2, shown in FIG. 7.

Figure 10:
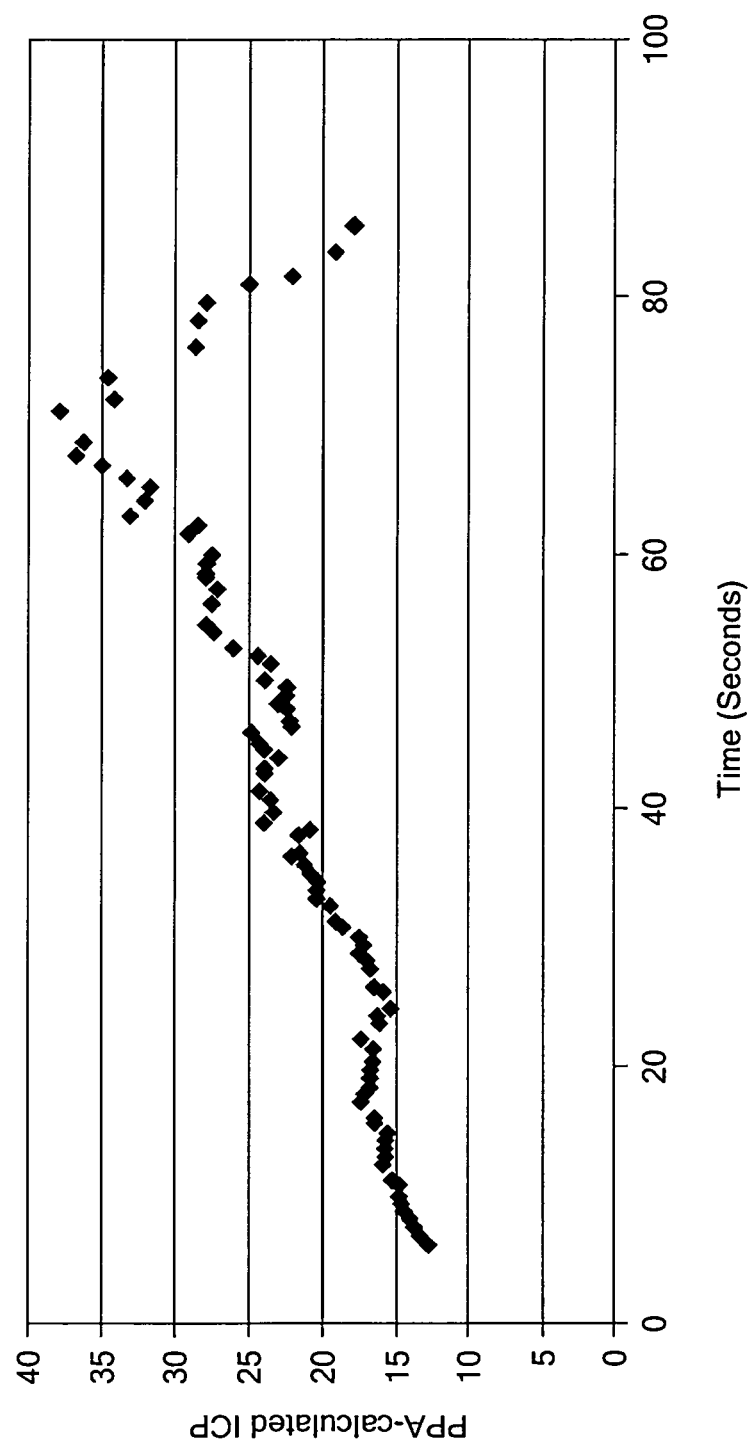
FIG. 10 is a graph showing exemplary test results of the non-invasive intracranial pressure system and method shown in one or more of FIGS. 2-9.

An initial demonstration of the non-invasive intracranial pressure monitoring system 20 and method thereof was conducted in an animal test. This test was used to verify that the ovine model was appropriate for the test and that non-invasive intracranial pressure monitoring system 20 can obtain the necessary data for calculating a measure of ICP. This early prototype utilized a laptop computer to acquire data from the first sensor 22, second sensor 24, and third sensor 26. The promising results are shown in FIG. 10.

Figure 11:
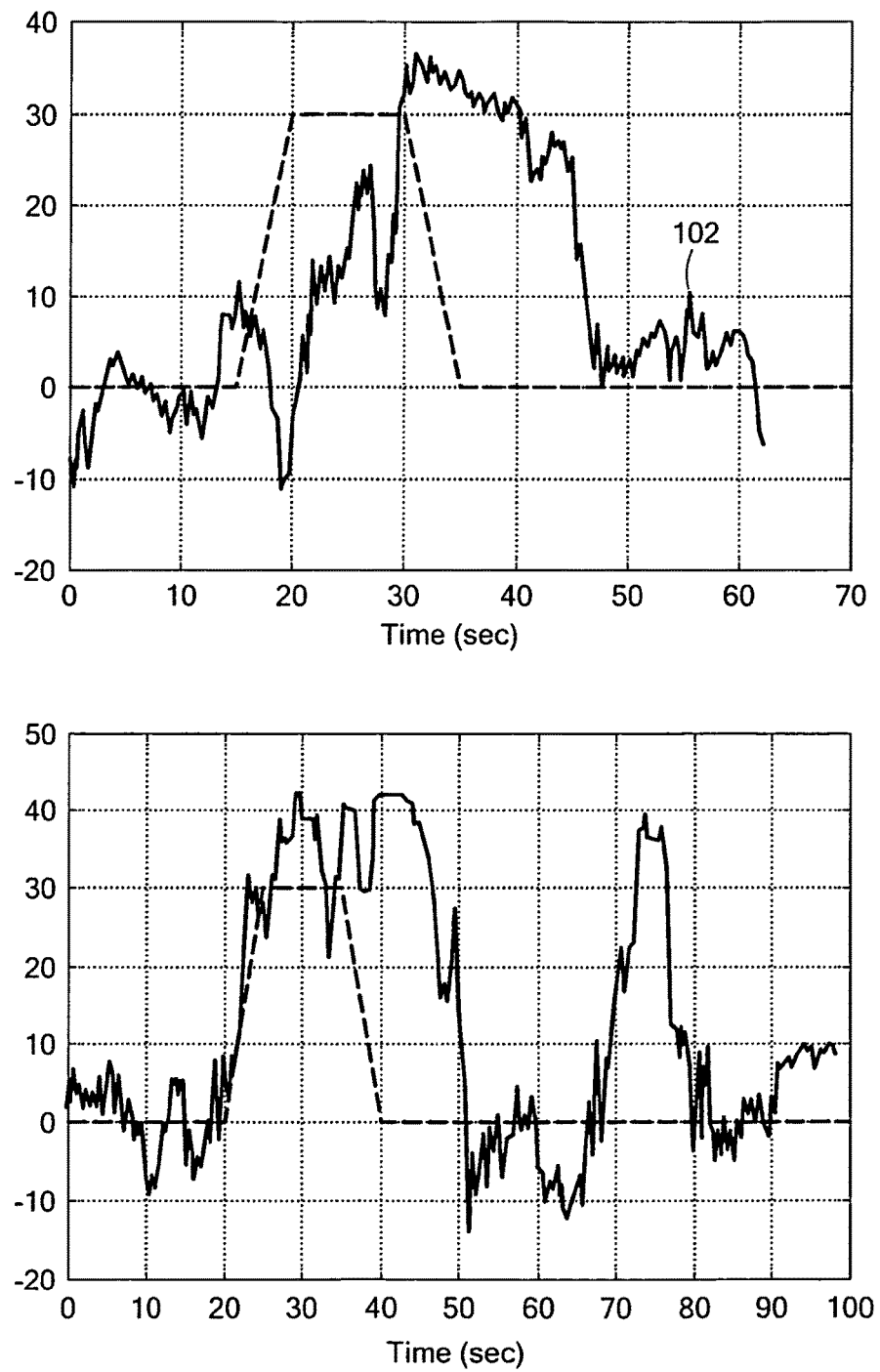
FIG. 11 shows graphs showing exemplary test results of the non-invasive intracranial pressure system and method shown in one or more of FIGS. 2-9.

With the preliminary ovine model completed, non-invasive intracranial pressure monitoring system 20 was further tested. The intracranial pressure of a subject was artificially increased due to hydrostatic pressure present in tilt from horizontal to upside down. FIG. 11 shows two such results from different subjects. Curve 100 indicates the tilt of the chair, from horizontal (zero) to upside down (recorded as 30). The value of 30 was assigned to the chair tilt as it is approximately the expected increase in the ICP, in cmH20, due to hydrostatic pressure. In the pilot study on healthy subjects, the exact value of the increase in ICP is unknown, and so the ICP algorithm was scaled by this value of 30 cm H20 across the data from all 6 subjects. In the second image shown in FIG. 11 (on the right), the inversion chair did not home properly and underwent a second, more rapid, inversion. Non-invasive intracranial pressure monitoring system 20 was able to determine the resultant increase in ICP in both excursions with high fidelity as seen in the image.

Figure 12:
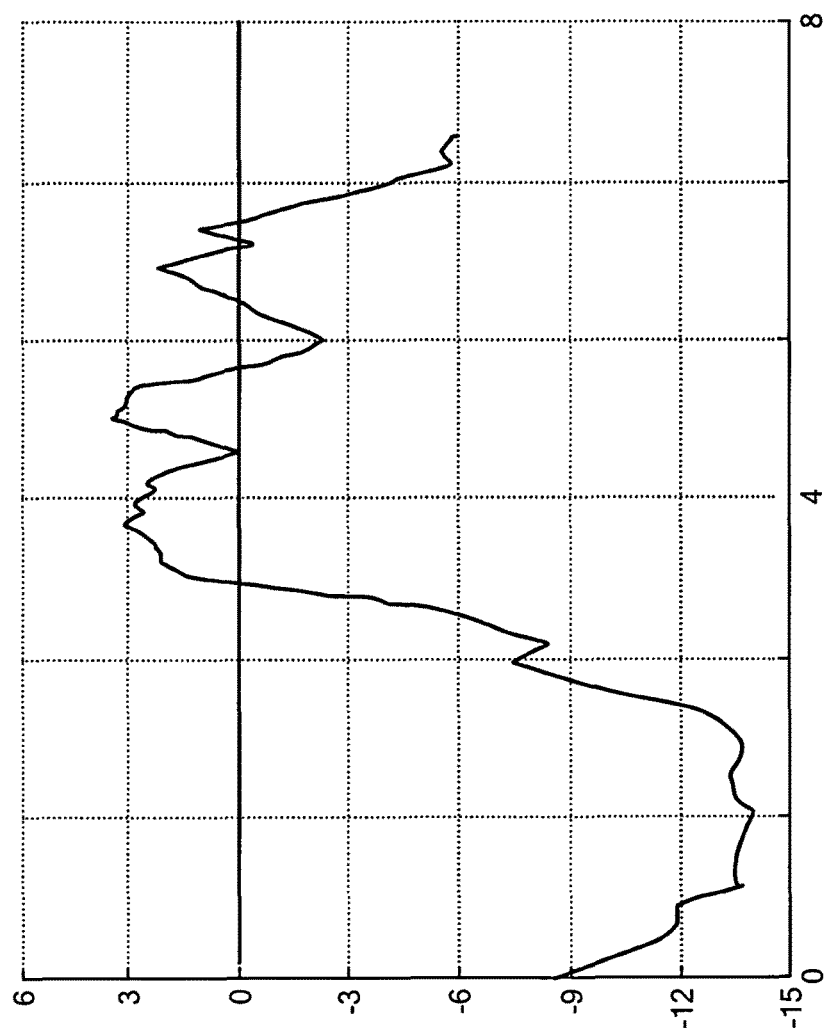
FIG. 12 is a graph showing exemplary test results of the non-invasive intracranial pressure system and method shown in one or more of FIGS. 2-9.

In a separate experiment, non-invasive intracranial pressure monitoring system 20 was used to record data during a squat-to-stand test (2 minutes of squat to straight standing). Non-invasive intracranial pressure monitoring system and the methods thereof discussed above with reference to one or more of FIGS. 2-9 was able to determine the negative value of ICP that is expected with such a test. The results are shown in FIG. 12.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A non-invasive intracranial pressure monitoring system comprising:
    a first sensor adapted to be placed proximate to a perfusion field of an artery receiving blood which emanates from the cranial cavity configured to monitor pulsations of the artery receiving blood which emanates from the cranial cavity artery;
    a second sensor adapted to be placed proximate to a perfusion field of an artery which does not receive blood emanating from the cranial cavity and placed approximately the same distance from the heart as the first sensor configured to monitor pulsations of the artery which does not receive blood emanating from the cranial cavity;
    a third sensor adapted to be placed distally from the heart configured to monitor pulsations of a distal artery; and
    a processing subsystem responsive to signals from the first, second, and third sensors configured to determine an indication of intracranial pressure by determining a first correlation between signals from the first sensor to signals from the third sensor and determining a second correlation between signals from the second sensor to signals from the third sensor and combining the determined first and second correlations.

2. The system of claim 1 in which the first sensor is placed on the forehead.

3. The system of claim 1 in which the second sensor is placed on the temple.

4. The system of claim 1 in which the second sensor is placed on the ear.

5. The system of claim 1 in which the third sensor is placed distally on a finger.

6. The system of claim 1 in which the third sensor is placed distally on a hand.

7. The system of claim 1 in which the third sensor is placed distally on a forearm.

8. The system of claim 1 further including a display coupled to the processing subsystem configured to display the intracranial pressure.

9. A non-invasive intracranial pressure monitoring system comprising:
    a first sensor adapted to be placed proximate to the supraorbital artery configured to monitor pulsations of the supraorbital artery;
    a second sensor adapted to be placed proximate to a branch of the external carotid artery and placed approximately the same distance from the heart as the first sensor configured to monitor pulsations of the external carotid artery;
    a third sensor adapted to be placed distally from the heart configured to monitor pulsations of a distal artery; and
    a processing subsystem responsive to signals from the first, second, and third sensors configured to determine an indication of intracranial pressure determining a first correlation between signals from the first sensor to signals from the third sensor and determining a second correlation between signals from the second sensor to signals from the third sensor and combining the determined first and second correlations.

10. The system of claim 9 in which the first sensor is adapted to be placed on the forehead.

11. The system of claim 9 in which the second sensor is adapted to be placed on the temple.

12. The system of claim 9 in which the second sensor is adapted to be placed on the ear.

13. The system of claim 9 in which the third sensor is adapted to be placed distally on a finger.

14. The system of claim 9 in which the third sensor is adapted to be placed distally on a hand.

15. The system of claim 9 in which the third sensor is adapted to be placed distally on a forearm.

16. The system of claim 9 further including a display coupled to the processing subsystem configured to display the intracranial pressure.

17. A method for non-invasively determining intracranial pressure, the method comprising:
    monitoring pulsations of an artery receiving blood which emanates from the cranial cavity with a first sensor and generating first output signals;
    monitoring pulsations of an artery which does not receive blood emanating from the cranial artery with a second sensor and generating second output signals;
    monitoring pulsations of a distal artery with a third sensor and generating third output signals; and
    in response to the first, second and third output signals, determining with a processing subsystem an indication of intracranial pressure by determining a first correlation between the first output signals from the first sensor to the third output signals from the third sensor and determining a second correlation between the second output signals from the second sensor to the third output signals from the third sensor and combining the determined first and second correlations.

18. The method of claim 17 in which said monitoring pulsations of blood which emanates from the cranial artery is performed proximate a forehead.

19. The method of claim 17 in which said monitoring pulsations of blood which does not emanate from a cranial artery is performed on the temple.

20. The method of claim 17 in which said monitoring pulsations of blood which does not emanate from a cranial artery is performed on the ear.

21. The method of claim 17 in which said monitoring pulsations of the distal artery is performed on a finger.

22. The method of claim 17 in which said monitoring pulsations of the distal artery is performed on a hand.

23. The method of claim 17 in which said monitoring pulsations of the distal artery is performed on a forearm.

24. A non-invasive method for determining intracranial pressure, the method comprising:
monitoring pulsations of the supraorbital artery with a first sensor and generating first output signals;
monitoring pulsations of the external carotid artery with a second sensor and generating second output signals;
monitoring pulsations of the distal artery with a third sensor and generating third output signals; and
in response to the first, second, and third output signals determining with a processing subsystem an indication of intracranial pressure by determining a first correlation between the first output signals from the first sensor to the third output signals from the third sensor and determining a second correlation between the second output signals from the second sensor to the third output signals from the third sensor and combining the determined first and second correlations.

25. The method of claim 24 in which said monitoring pulsations of the supraorbital artery is performed on the forehead.

26. The method of claim 24 in which monitoring pulsations of the external carotid artery is performed on the temple.

27. The method of claim 24 in which monitoring pulsations of the external carotid artery is performed on the ear.

28. The method of claim 24 in which monitoring pulsations of the distal artery is performed on a finger.

29. The method of claim 24 in which monitoring pulsations of the distal artery is performed on a hand.

30. The method of claim 24 in which monitoring pulsations of the distal artery is performed on a forearm.

* * * * *

UNITED STATES PATENT AND TRADEMARK OFFICE
CERTIFICATE OF CORRECTION

PATENT NO. : 9,826,913 B2
APPLICATION NO. : 13/939824
DATED : November 28, 2017
INVENTOR(S) : Anna M Galea Page 1 of 1

It is certified that error appears in the above-identified patent and that said Letters Patent is hereby corrected as shown below:

In the Specification

Column 1, Lines 7-11 reads "This invention was made with U.S. Government support under Contract No. N68335-10-C-0079, awarded by the Navy, and W81XWH-09-C-0118, awarded by the Army. The Government may have certain rights in certain aspects of the subject invention." Should read "This invention was made with U.S. Government support under Contract No. N68335-10-C-0079, awarded by the Navy, and W81XWH-09-C-0118, awarded by the Army. The Government has certain rights in the invention."

Signed and Sealed this
Twenty-sixth Day of November, 2019

Andrei Iancu
*Director of the United States Patent and Trademark Office*